(12) United States Patent
Petrucci et al.

(10) Patent No.: US 10,772,702 B2
(45) Date of Patent: Sep. 15, 2020

(54) SURGICAL LIGHTING APPARATUS INCLUDING SURGICAL LIGHTHEAD WITH MOVEABLE LIGHTING MODULES

(71) Applicant: American Sterilizer Company, Mentor, OH (US)

(72) Inventors: James Allyn Petrucci, Chesterland, OH (US); Lance Clark Bellows, Painesville, OH (US)

(73) Assignee: American Sterilizer Company, Mentor, OH (US)

( * ) Notice: Subject to any disclaimer, the term of this patent is extended or adjusted under 35 U.S.C. 154(b) by 139 days.

(21) Appl. No.: 16/223,234

(22) Filed: Dec. 18, 2018

(65) Prior Publication Data

US 2019/0282323 A1  Sep. 19, 2019

Related U.S. Application Data

(60) Provisional application No. 62/642,185, filed on Mar. 13, 2018.

(51) Int. Cl.
*A61B 90/35* (2016.01)
*F21V 14/02* (2006.01)
(Continued)

(52) U.S. Cl.
CPC .............. *A61B 90/35* (2016.02); *F21V 14/02* (2013.01); *F21V 21/15* (2013.01); *F21W 2131/205* (2013.01)

(58) Field of Classification Search
CPC ... A61B 90/35; F21V 14/02; F21W 2131/205
See application file for complete search history.

(56) References Cited

U.S. PATENT DOCUMENTS 1,880,399 A * 10/1932 Benjamin ............. F21V 7/0025
                                                    362/277
5,068,767 A * 11/1991 Koyama ................... F21S 2/00
                                                    315/152
(Continued)

FOREIGN PATENT DOCUMENTS

EP        1 741 975 A2    1/2007

OTHER PUBLICATIONS

International Search Report and Written Opinion issued in corresponding International Patent Application No. PCT/US2018/066352 dated Feb. 28, 2019.

*Primary Examiner* — Christian A Sevilla
(74) *Attorney, Agent, or Firm* — Kusner & Jaffe (57) ABSTRACT

A surgical lighting apparatus for illuminating a surgical environment includes a lighthead and a control unit. The control unit is configured to receive data from sensors positioned in one or more light emitting modules and identify, from the received data, an obstruction inhibiting delivery of a predetermined amount of light from one or more of light emitting elements of moveable light emitting modules to corresponding areas of a surgical site. The lighthead is configured to illuminate the surgical site. The lighthead includes a plurality of the light emitting modules and the sensors. Each of the light emitting modules includes a plurality of the light emitting elements positioned on a front side thereof. Each of the light emitting elements is configured to emit the predetermined amount of light from the light emitting modules to illuminate one of the corresponding areas of the surgical site.

20 Claims, 7 Drawing Sheets

(51) Int. Cl.
*F21V 21/15* (2006.01)
*F21W 131/205* (2006.01)

(56) References Cited

U.S. PATENT DOCUMENTS

| | | | | |
|---|---|---|---|---|
| 6,582,092 B1* | 6/2003 | Marka | F21V 14/04 | 362/319 |
| 6,803,727 B2* | 10/2004 | Laerum | H05B 45/20 | 315/129 |
| 6,857,772 B2* | 2/2005 | Brukilacchio | F21V 29/67 | 362/572 |
| 7,210,810 B1* | 5/2007 | Iversen | A61B 90/35 | 362/105 |
| 7,922,347 B2* | 4/2011 | Kaletin | A61B 90/30 | 362/33 |
| 8,657,464 B2* | 2/2014 | Lundberg | F21S 10/023 | 362/232 |
| 9,016,916 B2* | 4/2015 | Marka | F21V 23/04 | 362/572 |
| 9,629,220 B2* | 4/2017 | Panopoulos | H05B 47/105 | |
| 9,746,159 B1* | 8/2017 | Fletcher | F21V 14/02 | |
| 9,752,752 B2* | 9/2017 | Gassner | F21S 8/06 | |
| 2009/0046146 A1* | 2/2009 | Hoyt | H04N 7/18 | 348/143 |
| 2011/0105851 A1* | 5/2011 | Horvath | H05B 47/28 | 600/249 |
| 2012/0259178 A1* | 10/2012 | Kim | A61B 90/30 | 600/249 |
| 2014/0015948 A1* | 1/2014 | Tam | A61B 90/35 | 348/77 |
| 2014/0334133 A1* | 11/2014 | Ferguson | F21V 33/0068 | 362/105 |
| 2014/0346957 A1* | 11/2014 | Micucci | G06F 3/017 | 315/152 |
| 2015/0035437 A1* | 2/2015 | Panopoulos | H05B 47/19 | 315/112 |
| 2015/0055323 A1* | 2/2015 | Schreiber | F21V 21/30 | 362/96 |
| 2015/0369455 A1* | 12/2015 | Nieminen | F21S 8/06 | 362/428 |
| 2016/0131356 A1* | 5/2016 | Engberg | F21V 14/02 | 362/373 |
| 2017/0038046 A1* | 2/2017 | Bardot | F21V 21/30 | |
| 2017/0167702 A1* | 6/2017 | Mariampillai | F21V 9/14 | |
| 2017/0318644 A1* | 11/2017 | Hartl | H05B 47/105 | |
| 2017/0367785 A1* | 12/2017 | Munari | H05B 45/20 | |
| 2019/0201046 A1* | 7/2019 | Shelton, IV | G16H 50/20 | |
| 2019/0201137 A1* | 7/2019 | Shelton, IV | A61B 5/0075 | |
| 2019/0201594 A1* | 7/2019 | Shelton, IV | A61B 5/0075 | |
| 2020/0060785 A1* | 2/2020 | Chandan | F21V 21/403 | |
| 2020/0166198 A1* | 5/2020 | Vidakovic | F21V 17/12 | |

\* cited by examiner

FIG. 7

SURGICAL LIGHTING APPARATUS INCLUDING SURGICAL LIGHTHEAD WITH MOVEABLE LIGHTING MODULES

RELATED APPLICATION

This application claims the benefit of U.S. Provisional Application No. 62/642,185, filed on Mar. 13, 2018, the entire contents of which are incorporated herein by reference.

FIELD OF THE INVENTION

The present invention relates generally to the art of surgical lighting, and, more particularly, to a surgical lighting apparatus having a surgical lighthead having lighting modules that are enabled to illuminate a surgical site and move in response to a detection of obstructions blocking illumination of the surgical site by the lighting modules.

BACKGROUND OF THE INVENTION

Surgical lighting systems are used to illuminate surgical sites placed in surgical environments. A common concern for such systems is how best to handle obstructions that block light supplied for illuminating surgical sites. Such obstructions are typically caused by movement of surgical team members between the lighting elements of a system and the surgical site. Such instances are commonly solved by reducing the light intensity of obstructed lighting elements and increasing the light intensity of unobstructed lighting elements.

However, redistributing the light intensity to the unobstructed lighting elements does not address the obstruction of the other lighting elements. As such, illumination provided to the surgical site as a whole is significantly reduced. The surgical site may also be subject to a proliferation of shadows created by the obstructions. Redistributing the light intensity to the unobstructed lighting elements also reduces the life span of those lighting elements compared with the obstructed lighting elements. There is also an increase in heat emitted from the intensified unobstructed lighting elements.

The present invention provides an improved system for illuminating a surgical site when obstructions are formed between the lighting elements and the surgical site.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF THE INVENTION

Figure 1:
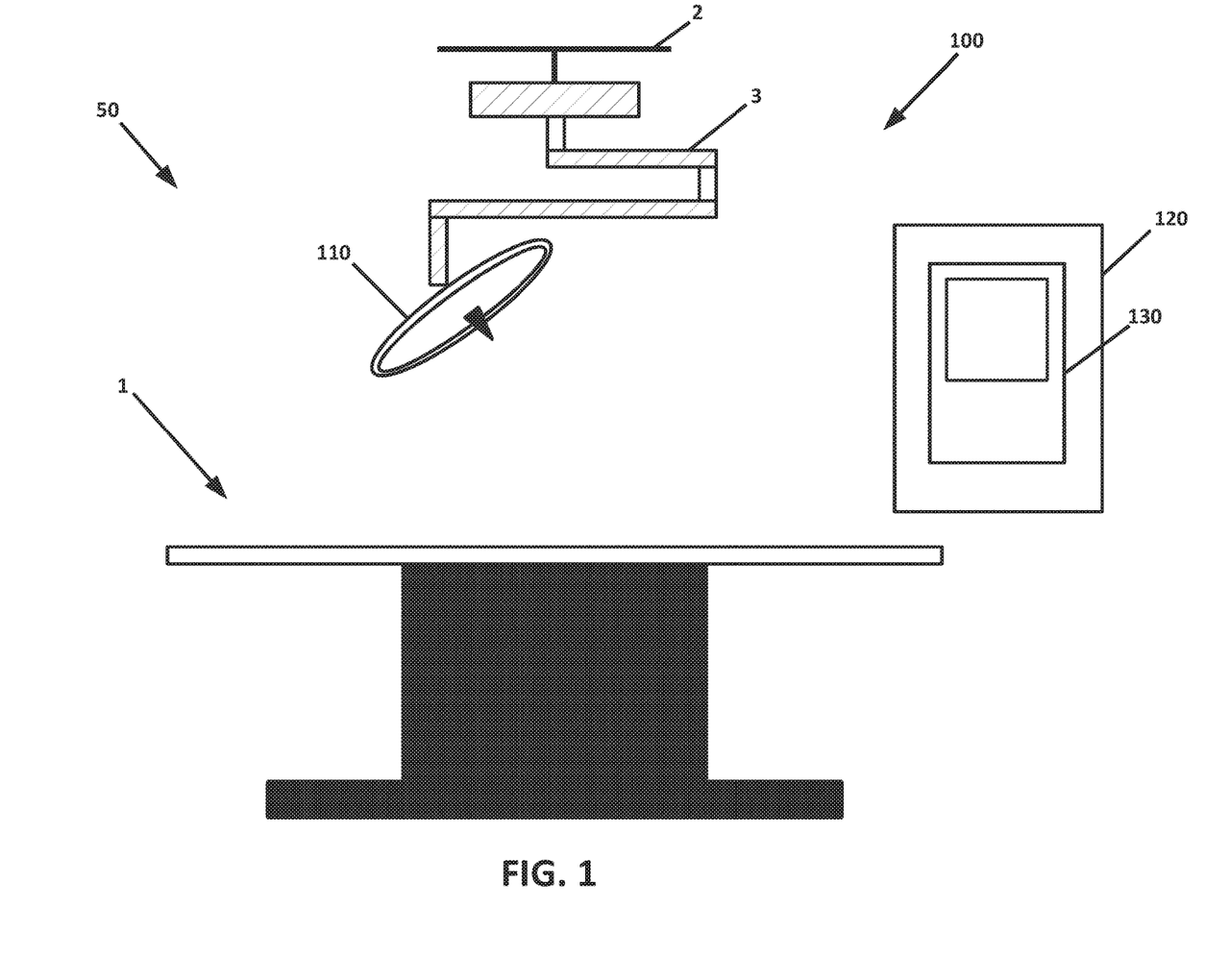
FIG. 1 is a schematic view of an example surgical lighting apparatus positioned in a surgical environment according to a first embodiment of the present invention.
Figure 2:
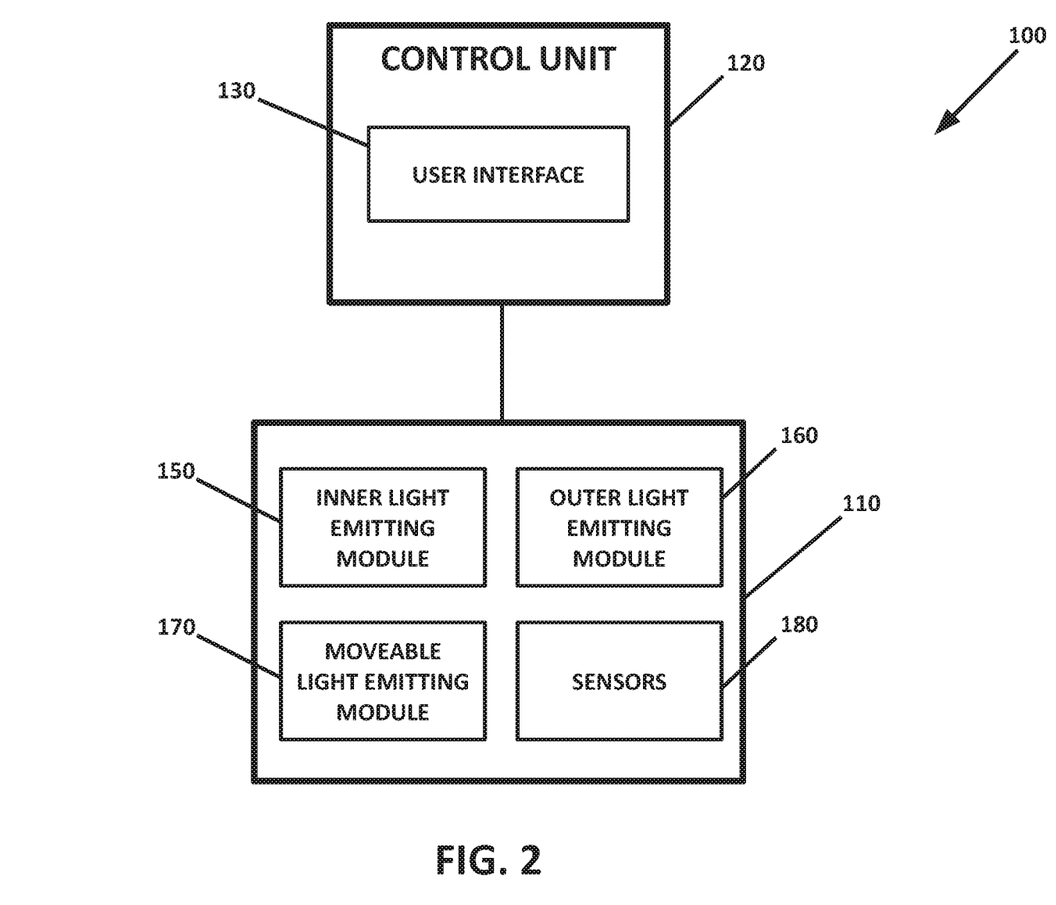
FIG. 2 is a block diagram of a surgical lighting apparatus according to a first embodiment of the present invention.
Figure 3:
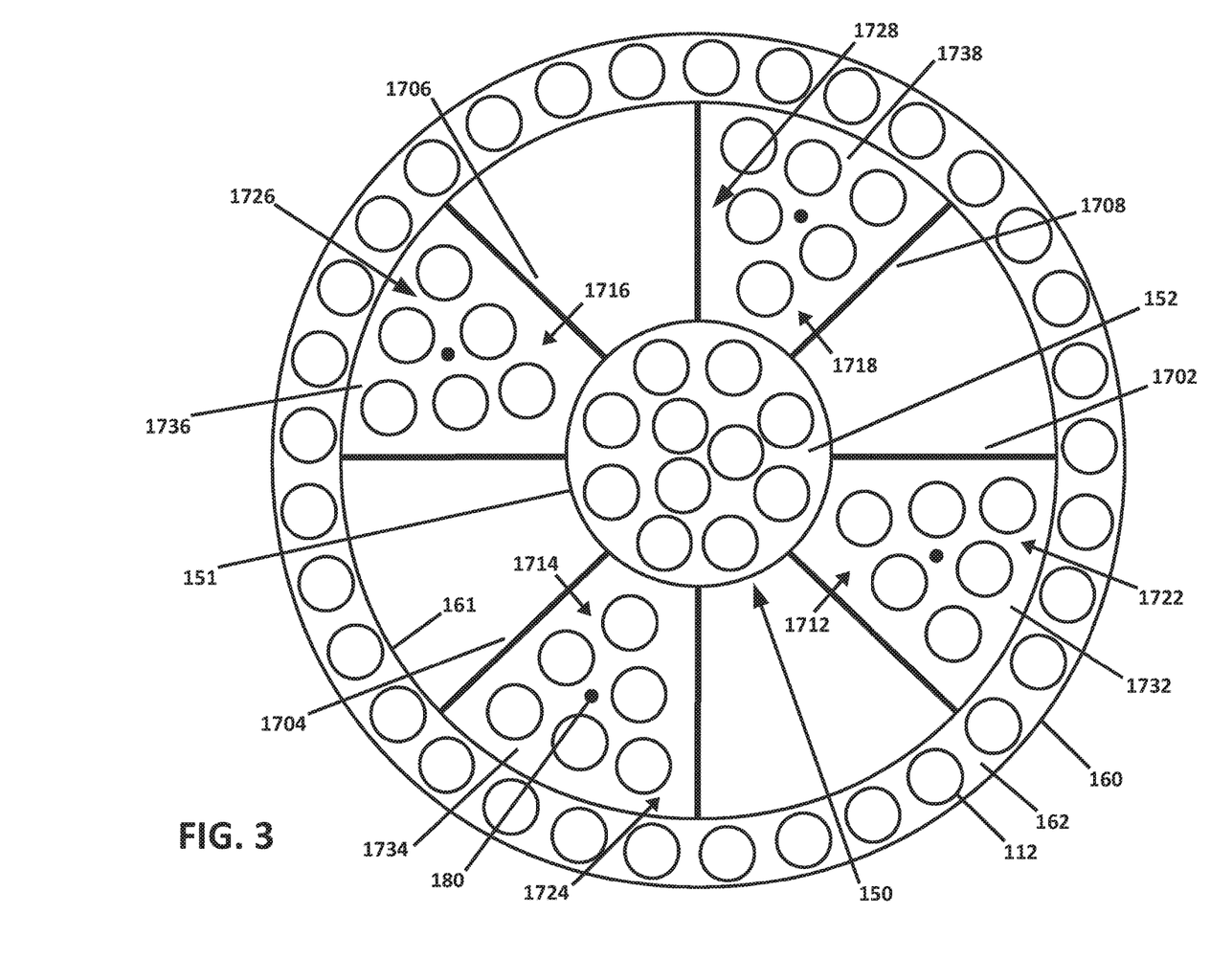
FIG. 3 is a front view of a lighthead of a surgical lighting apparatus according to a first embodiment of the present invention.

Referring now to the drawings wherein the showings are for illustrating example embodiments of the invention only and not for limiting same, FIG. 1 shows a surgical lighting apparatus 100 for a surgical environment 50 according to a first embodiment of the present invention. As is illustrated in FIGS. 1-3, surgical lighting apparatus 100 includes a lighthead 110 and a control unit 120. Lighthead 110 is configured to illuminate a surgical site 1 disposed in surgical environment 50.

Lighthead 110 is mounted to a ceiling 2 of surgical environment 50 by a lighthead mounting arm 3. Lighthead mounting arm 3 is moveable to position lighthead 110 as desired. Lighthead mounting arm 3 may be moved manually. Lighthead mounting arm 3 may also be motorized to move at the request of control unit 120. Control unit 120 may include a user interface 130. User interface 130 may enable a user to control positioning of lighthead mounting arm 3 through control unit 120. Control unit 120 and user interface 130 will be detailed more specifically in the discussion below.

Lighthead 110 includes stationary light emitting modules 150 and 160, moveable light emitting modules 170, and sensors 180. A center light emitting module 150 and an outer light emitting module 160 constitute the stationary light emitting modules of lighthead 110. Moveable light emitting modules 170 may be positioned between center light emitting module 150 and outer light emitting module 160. As illustrated in FIGS. 3-6, lighthead 110 may include multiple moveable light emitting modules 1702, 1704, 1706, and 1708.

Each of center light emitting module 150, outer light emitting module 160, and moveable light emitting modules 1702, 1704, 1706, and 1708 is equipped with a plurality of light emitting elements 112 respectively positioned on front sides 152, 162, 1732, 1734, 1736, and 1738 thereof. Each of light emitting elements 112 is enabled to emit a predetermined amount of light to illuminate an area of surgical site 1 corresponding with a respective position of light emitting element 112.

As illustrated in FIGS. 3-6, center light emitting module 150 may have an outer circumference 151, and outer light emitting module 160 may have an inner circumference 161 facing outer circumference 151 of center light emitting module 150. Moveable light emitting modules 1702, 1704, 1706, and 1708 are enabled to respectively move about outer circumference 151 of center light emitting module 151 and within inner circumference 161 of outer light emitting module 160.

Figure 5:
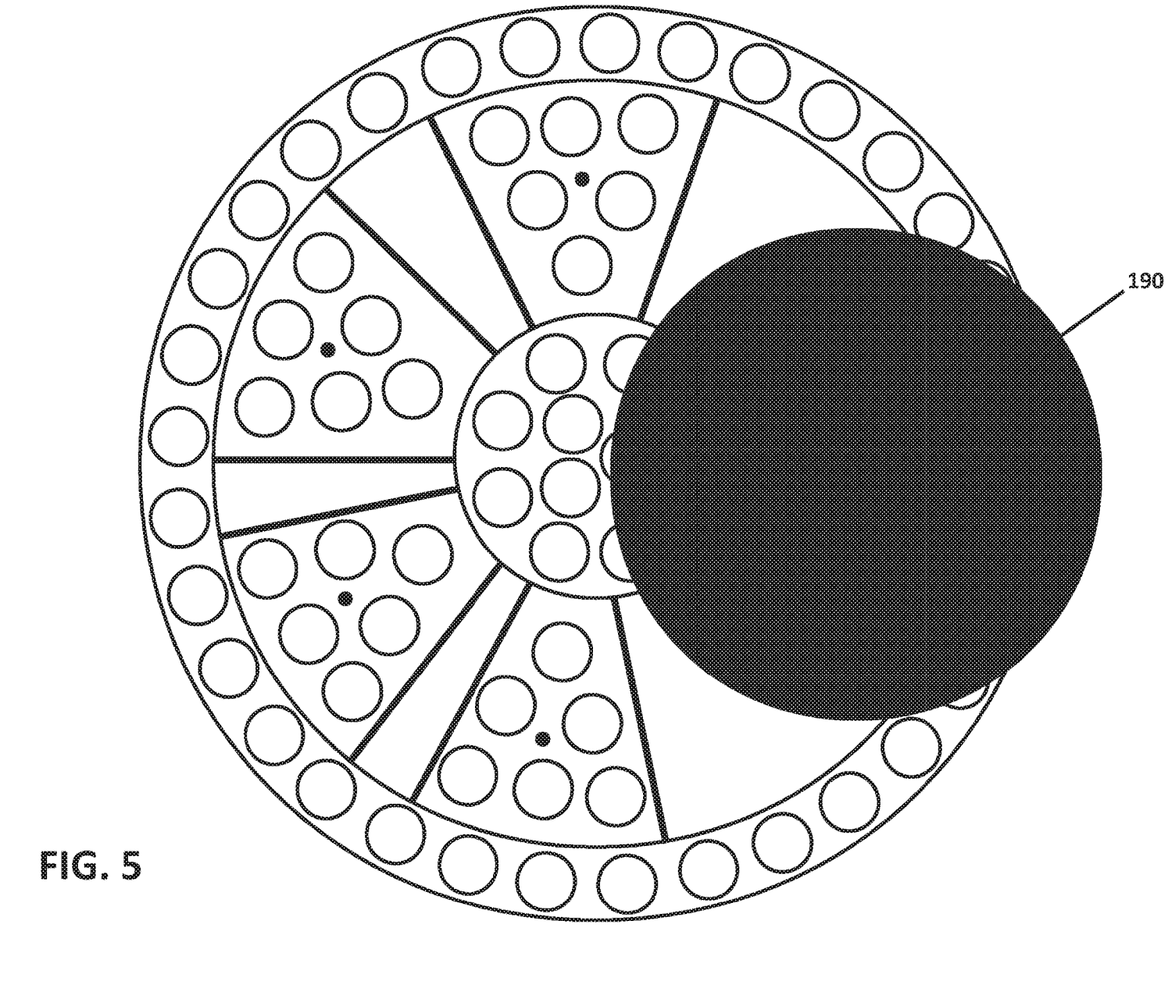
FIG. 5 is a front view of a lighthead of a surgical lighting apparatus according to a first embodiment of the present invention, in which an obstruction is positioned between a lighthead and a surgical site.
Figure 6:
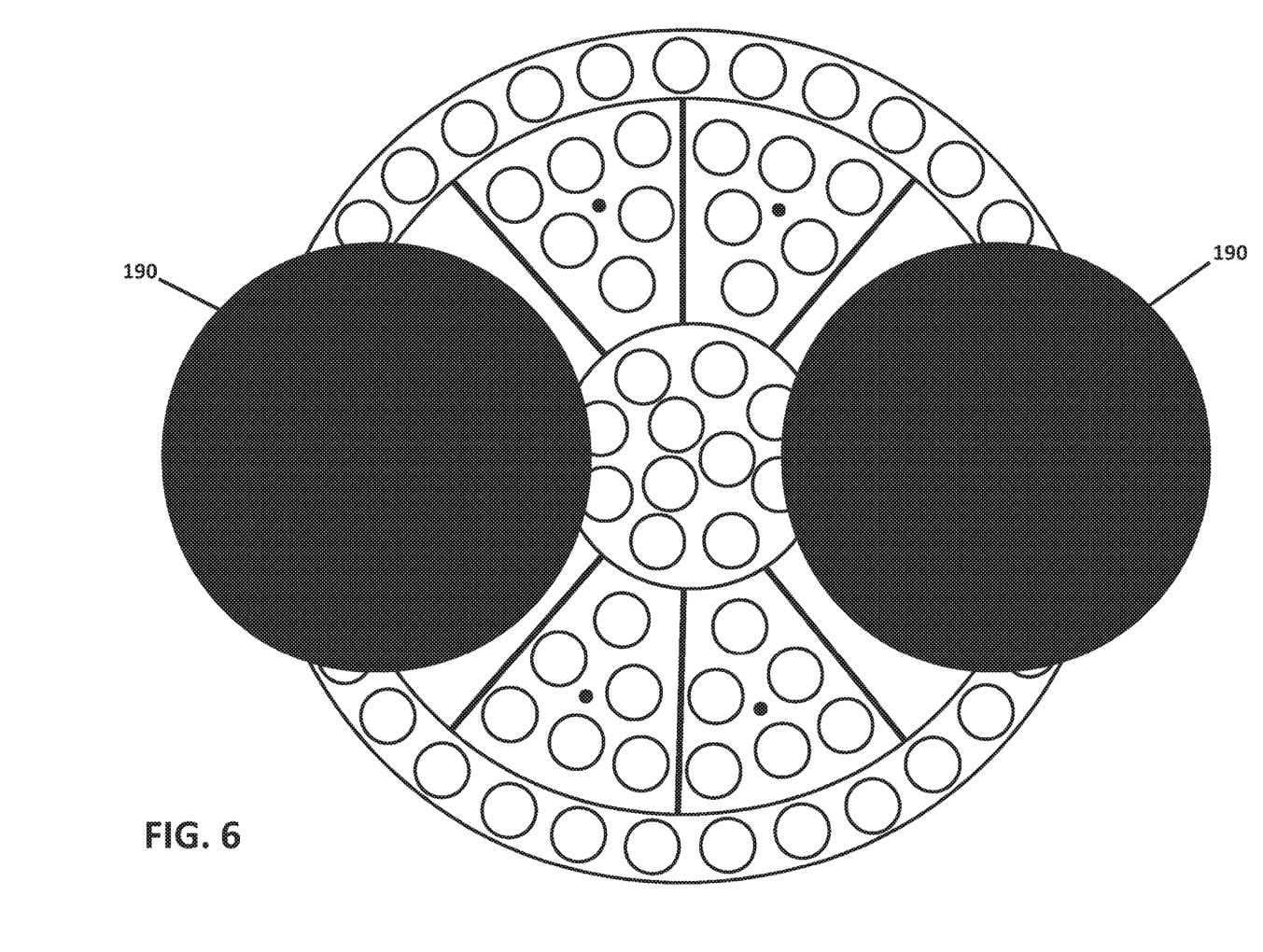
FIG. 6 is a front view of a lighthead of a surgical lighting apparatus according to a first embodiment of the present invention, in which multiple obstructions are positioned between a lighthead and a surgical site.

As is illustrated in FIGS. 3, 5, and 6, each of moveable light emitting modules 1702, 1704, 1706, and 1708 is positioned between two other moveable light emitting modules 1702, 1704, 1706, and 1708. For example, moveable light emitting module 1702 is positioned between moveable light emitting module 1704 and moveable light emitting module 1708.

Each of moveable light emitting modules 1702, 1704, 1706, and 1708 is enabled to move between the two other moveable light emitting modules 1702, 1704, 1706, and 1708. In other words, as applied in our example above, moveable light emitting module 1702 is enabled to move between moveable light emitting module 1704 and moveable light emitting module 1708. As such, because of the design of moveable light emitting modules 1702, 1704, 1706, and 1708, none of moveable light emitting modules 1702, 1704, 1706, and 1708 is able to move 180° about outer circumference 151 of center light emitting module 151 or 180° within inner circumference 161 of outer light emitting module 160. This preserves a constant area of open space between center light emitting module 150, outer light emitting module 160, and moveable light emitting modules 1702, 1704, 1706, and 1708, which subsequently preserves laminar airflow through the constant area.

Moveable light emitting modules 1702, 1704, 1706, and 1708 may respectively have inner edges 1712, 1714, 1716, and 1718 and outer edges 1722, 1724, 1726, and 1728. Inner edges 1712, 1714, 1716, and 1718 may be positioned adjacent outer circumference 151 of center light emitting module 150. Outer edges 1722, 1724, 1726, and 1728 may be positioned adjacent inner circumference 161 of outer light emitting module 160.

Inner edges 1712, 1714, 1716, and 1718 may be moveably secured to outer circumference 151 of center light emitting module 150. The means by which inner edges 1712, 1714, 1716, and 1718 are secured to outer circumference 151 of center light emitting module 150 could be any appropriate means known to those having ordinary skill in the art.

For example, a ring could be mounted to outer circumference 151 of center light emitting module 150. Inner edges 1712, 1714, 1716, and 1718 of moveable light emitting modules 1702, 1704, 1706, and 1708 could be equipped with a bore running therethrough. The bores of the inner edges 1712, 1714, 1716, and 1718 could be mounted around the ring such that the ring runs through the bore and the bore allows each of moveable light emitting modules 1702, 1704, 1706, and 1708 to move along the ring. However, embodiments disclosed herein are not limited thereto.

Figure 4:
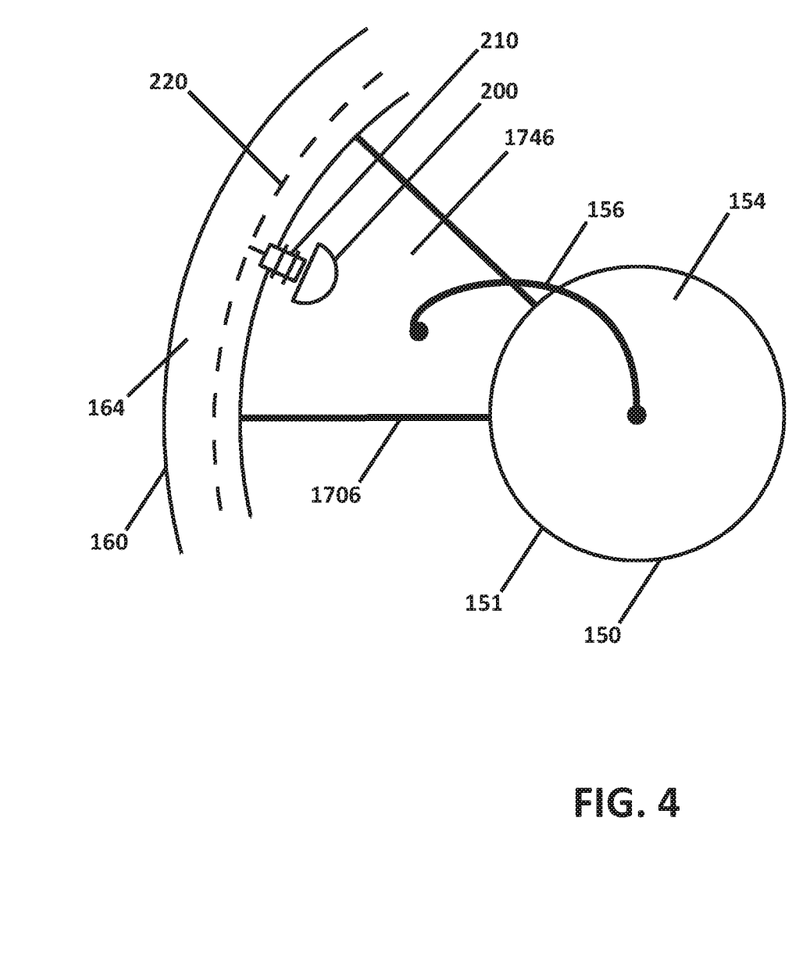
FIG. 4 is a partial rear view of a lighthead of a surgical lighting apparatus according to a first embodiment of the present invention.

The partial rear view of lighthead 110 illustrated in FIG. 4 is directed to respective rear sides 154, 164, and 1746 of center light emitting module 150, outer light emitting module 160, and moveable light emitting module 1706. Rear side 1746 of moveable light emitting module 1706 is characteristic of the rear sides of moveable light emitting modules 1702, 1704, and 1708. As such, only rear side 1746 of moveable light emitting module 1706 will be described.

A motor 200 is mounted on rear side 1746 of moveable light emitting module 1706 at outer edge 1726 thereof. Motor 200 has a motor gear 210 mounted thereto. Motor gear 210 may be a spur gear, but is not limited thereto. Motor gear 210 may be any applicable gear known to one having ordinary skill in the art for such use.

Motor gear 210 engages a panel gear 220 positioned on rear side 164 of outer light emitting module 160. Panel gear 220 may be a planetary gear running around a circumference of rear side 164 of outer light emitting module 160. However, embodiments described herein may not be limited thereto. Panel gear 220 may be any applicable gear known to one having ordinary skill in the art for such use.

Motor 200 is enabled to move motor gear 210 engaged with panel gear 220 clockwise or counter-clockwise to move moveable light emitting module 1706 in either respective direction about outer circumference 151 of center light emitting module 150 and within inner circumference 161 of outer light emitting module 160. Using the previously introduced example, motor 200 is also enabled to move motor gear 210 engaged with panel gear 220 to move moveable light emitting module 1706 on which motor 200 is mounted to move between moveable light emitting module 1704 and moveable light emitting module 1708.

Power and function is provided to power light emitting elements 112 and motor 200 of moveable light emitting module 1706 from an electrical connection 156, which extends from rear side 154 of center light emitting module 150 to rear side 1746 of moveable light emitting module 1706. The means by which electrical connection 156 provides power and function to moveable light emitting module 1706 may be that of any standard wiring mechanism known to those having ordinary skill in the art.

Moveable light emitting modules 1702, 1704, and 1708 are respectively provided power and function through electrical connections in the same way electrical connection 156 provides power and function to moveable light emitting module 1706. However, it is particularly required for all electrical connections to be arranged such that an electrical connection of one of the moveable light emitting modules does not interfere with the movement or the electrical connection of any other of moveable light emitting modules 1702, 1704, and 1708. As such, movement of moveable light emitting module 1706 will not affect the ability of moveable light emitting modules 1702, 1704, and 1708 to be simultaneously and independently moved and controlled through respective electrical connections.

Movement of motor 200 of moveable light emitting module 1706, as well as moveable light emitting modules 1702, 1704, and 1708, is provided by control unit 120, which will be explained in further detail below.

Sensors 180 are enabled to collect data regarding an amount of the emitted light from each of light emitting elements 112 that illuminates the corresponding area of surgical site 1. In other words, sensors 180 are enabled to collect data that could lead to identification of one or more obstructions 190, of which examples are illustrated in FIGS. 5 and 6. Sensors 180 are further enabled to transmit the collected data to control unit 120. While sensors 180 are shown as being provided in at least one of light emitting modules 150, 160, and 170, embodiments disclosed herein are not limited thereto. Specifically, sensors 180 are positioned to allow the aforementioned data collection to take place in an optimal manner.

Referring to a first embodiment of the present invention illustrated in FIGS. 2, 3, 5, and 6, one of sensors 180 are positioned in each of moveable light emitting modules 1702, 1704, 1706, and 1708. In this example, taking into account FIG. 4, power, at the minimum, would be provided to sensor 180 of moveable light emitting module 1706 by electrical connection 156. It is conceivable that function and data transmittal could be accomplished either through wireless means known to those having ordinary skill in the art or through electrical connection 156.

Figure 7:
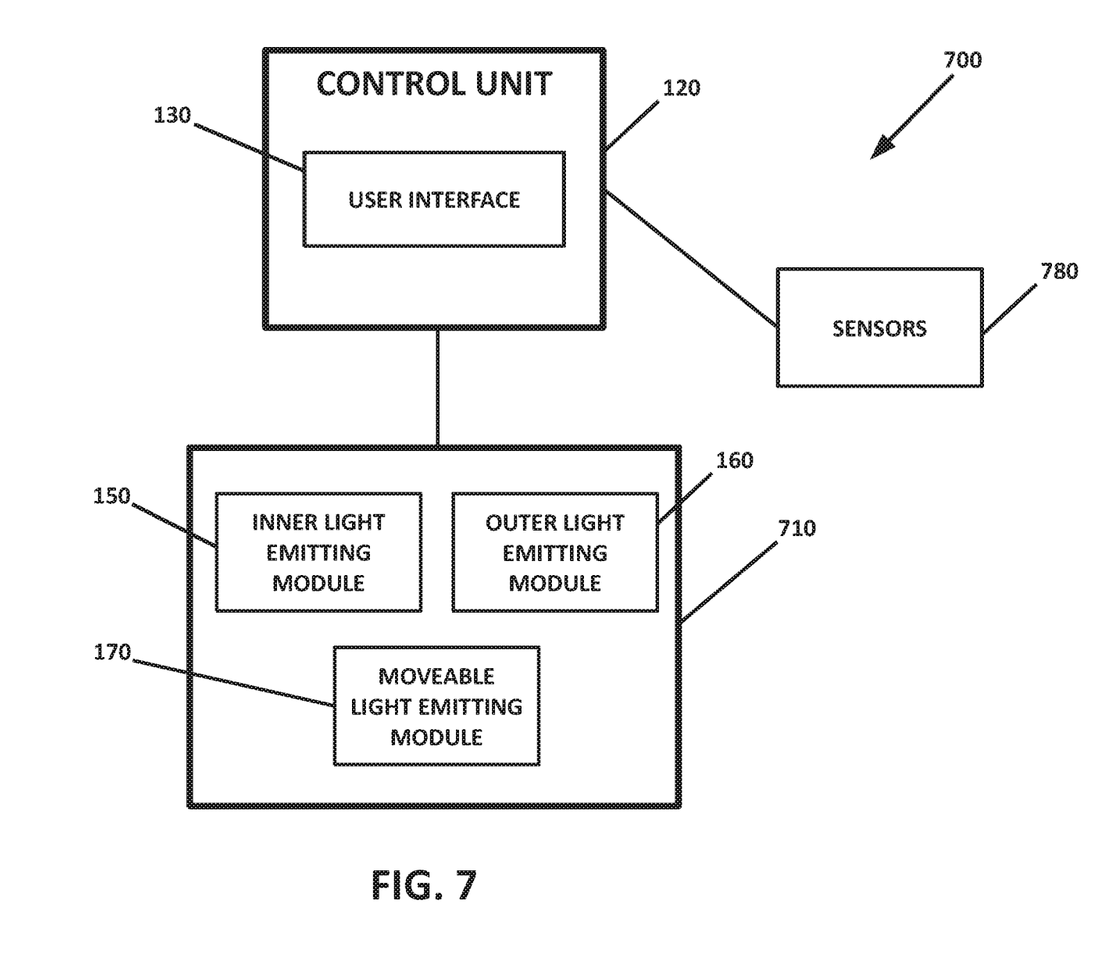
FIG. 7 is a block diagram of a surgical lighting apparatus according to a second embodiment of the present invention.

Referring now to a second embodiment of the present invention illustrated in FIG. 7, a surgical lighting apparatus 700 is essentially the same as surgical lighting apparatus 100 of the first embodiment of the present invention described above. However, in surgical lighting apparatus 700, sensors 780 are not included in a lighthead 710. Instead, sensors 780 are remotely positioned from lighthead 710 at another location within surgical environment 50. In this case, data transmittal and power would be provided to sensors 780 through other wireless or wired means.

Just as is the case with sensors 180, sensors 780 are enabled to collect data regarding an amount of the emitted light from each of light emitting elements 112 that illuminates the corresponding area of surgical site 1. In other words, sensors 780 are enabled to collect data that could lead to identification of one or more obstructions 190, of which examples are illustrated in FIGS. 5 and 6. Sensors 780 are further enabled to transmit the collected data to control unit 120.

Another embodiment is contemplated that includes both sensors 180 and 780. For example, sensors 180 may be included in multiple light emitting modules 150, 160, and 170 of lighthead 110 at the same time that sensors 780 are positioned remotely from lighthead 110.

Referring to illustrations provided in FIGS. 1, 2, and 5-7, control unit 120 is enabled to receive the data transmitted collected from sensors 180 and 780 and identify, from the received data, at least one obstruction 190 inhibiting delivery of the predetermined amount of light from one or more of light emitting elements 112 of moveable light emitting modules 1702, 1704, 1706, and 1708 to the corresponding areas of surgical site 1. In addition, as was previously mentioned, control unit 120 is further enabled to control movement of one or more of moveable light emitting modules 1702, 1704, 1706, and 1708 to respective positions. The positions to which the one or more moveable light emitting modules 1702, 1704, 1706, and 1708 are moved to allow for illumination of corresponding areas of surgical site 1 by the emitted predetermined amount of light without inhibition by obstruction 190.

For example, as previously noted, obstructions 190 can be formed in various ways, such as, but not limited, blockages created by surgical staff. When one of obstructions 190 is formed, sensors 180 and 780 collect data that, when analyzed by control unit 120, will indicate an area of surgical site 1 as not receiving the predetermined amount of light from corresponding light emitting elements 112. Control unit 120 will then determine that a light deficiency exists in areas of surgical site 1. Control unit 120 will further determine that the light deficiency is attributable to an absence of light from light emitting elements 112 of one or more of moveable light emitting modules 1702, 1704, 1706, and 1708. After additional analysis, including analysis related to the shape and size of the cumulative area of surgical site 1 in which light is deficient, control unit 120 will identify the absence of light as being caused by one or more obstructions 190 inhibiting respective delivery of the predetermined amount of light from light emitting elements 112 of moveable light emitting modules 1702, 1704, 1706, and 1708 to the corresponding areas of surgical site 1.

Upon the identification of obstructions 190, control unit 120 determines optimal positions to which to one or more of moveable light emitting modules 1702, 1704, 1706, and 1708 should be moved to overcome the blockage of obstructions 190. This determination includes the identification of optimal directions in which to respectively move one or more of moveable light emitting modules 1702, 1704, 1706, and 1708 about outer circumference 151 of center light emitting module 150 to arrive at those optimal positions. Subsequently, control unit 120 is enabled to move motor gears 210 of the one or more moveable light emitting modules 1702, 1704, 1706, and 1708 in the optimal directions to move the one or more moveable light emitting modules 1702, 1704, 1706, and 1708 to the respectively optimal positions. Movement of the obstructed moveable light emitting modules 1702, 1704, 1706, and 1708 to the optimal positions will allow corresponding areas of surgical site 1 to be illuminated by the emitted predetermined amount of light of the one or more of light emitting elements 112 without inhibition by obstructions 190.

Along with enabling a user to specify a position at which one of lightheads 110 and 710 will be oriented by lighthead mounting arm 3, user interface 130 is enabled to permit user input of the predetermined amount of light to be emitted from each of light emitting elements 112 to illuminate the corresponding area of surgical site 1. User interface 130 is also enabled to allow a user to specify a light deficiency percentage at which control unit 120 is to recognize the existence of obstructions 190. User interface 130 is further enabled to allow a user to specify the extent to which moveable light emitting modules 1702, 1704, 1706, and 1708 will move upon identification of obstructions 190 respectively corresponding with light emitting elements 112 positioned thereon. User interface 130 may also allow user to specify an amount of time that moveable light emitting modules 1702, 1704, 1706, and 1708 will remain in the optimal positions after obstructions 190 are no longer identified by control unit 120.

The foregoing descriptions are example embodiments of the present invention. It should be appreciated that these embodiments are described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

The invention claimed is:

1. A surgical lighting apparatus for a surgical environment, the apparatus comprising:
 a lighthead configured to illuminate a surgical site disposed in the surgical environment, the lighthead comprising:
  a plurality of light emitting modules, each of the light emitting modules comprising a plurality of light emitting elements positioned on a front side thereof, each of the light emitting elements being configured to emit a predetermined amount of light from the light emitting modules to illuminate a corresponding area of a surgical site, the light emitting modules being comprised of a plurality of stationary light emitting modules and a plurality of moveable light emitting modules; and
  sensors positioned in one or more of the light emitting modules, the sensors being configured to collect data regarding an amount of the emitted light from each of the light emitting elements that is delivered to the corresponding area of the surgical site, the sensors being further configured to transmit the collected data; and
 a control unit configured to receive the transmitted data from the sensors and identify, from the received data, an obstruction inhibiting respective delivery of the predetermined amount of light from one or more of the light emitting elements of the moveable light emitting modules to the corresponding areas of the surgical site, the control unit being further configured to control movement of one or more of the moveable light emitting modules to respective positions at which the corresponding areas of the surgical site are illuminated by the emitted predetermined amount of light of the one or more of the light emitting elements of the moveable light emitting modules without inhibition by the obstruction.

2. The apparatus of claim 1, wherein the stationary light emitting modules comprise a center light emitting module and an outer light emitting module, and
wherein the moveable light emitting modules are positioned between the center light emitting module and the outer light emitting module.

3. The apparatus of claim 2, wherein the center light emitting module has an outer circumference and an outer light emitting module has an inner circumference facing the outer circumference of the center light emitting module, and
wherein the moveable light emitting modules are configured to respectively move about the outer circumference of the center light emitting module and within the inner circumference of the outer light emitting module.

4. The apparatus of claim 3, wherein each of the moveable light emitting modules is positioned between two of the moveable light emitting modules, and
wherein each of the moveable light emitting modules is configured to move between the two of the moveable light emitting modules.

5. The apparatus of claim 4, wherein the moveable light emitting modules are configured to respectively move less than 180° about the outer circumference of the center light emitting module or within the inner circumference of the outer light emitting module.

6. The apparatus of claim 4, wherein a constant area of open space between the center light emitting module, the outer light emitting module, and the moveable light emitting modules is preserved to ensure laminar airflow through the constant area.

7. The apparatus of claim 3, wherein each of the moveable light emitting modules comprises an inner edge and an outer edge, the inner edge being positioned adjacent the outer circumference of the center light emitting module, the outer edge being positioned adjacent the inner circumference of the outer light emitting module, and
wherein the inner edge of the moveable light emitting module is moveably secured to the outer circumference of the center light emitting module.

8. The apparatus of claim 7, wherein a motor is positioned on a rear side of each of the moveable light emitting modules at the outer edge thereof,
wherein a motor gear is mounted on each of the motors,
wherein each of the motor gears engages a panel gear positioned on a rear side of the outer light emitting module, and
wherein each of the motors is configured to move the motor gear engaged with the panel gear to move the moveable light emitting module about the outer circumference of the center light emitting module and within the inner circumference of the outer light emitting module.

9. The apparatus of claim 8, wherein each of the moveable light emitting modules is positioned between two of the moveable light emitting modules, and
wherein each of the motors is configured to move the motor gear engaged with the panel gear to move the moveable light emitting module on which the motor is mounted between the two of the moveable light emitting modules.

10. The apparatus of claim 8, wherein power and control is respectively provided to the motors of the moveable light emitting modules by electrical connections independently extending between the moveable light emitting modules and the center light emitting module.

11. The apparatus of claim 8, wherein each of the motors is controlled individually by the control unit.

12. The apparatus of claim 1, wherein the sensors respectively transmit the collected data to the control unit.

13. The apparatus of claim 1, wherein each of the moveable light emitting modules includes at least one of the sensors.

14. The apparatus of claim 10, wherein each of the moveable light emitting modules includes at least one of the sensors, and
wherein the power is respectively provided to the sensors of the moveable light emitting modules by the independently extending electrical connections.

15. The apparatus of claim 14, wherein the sensors respectively communicate with the control unit through the independently extending electrical connections.

16. The apparatus of claim 1, wherein the sensors are positioned in one or more of the moveable light emitting modules.

17. The apparatus of claim 1, wherein the control unit is further configured to determine optimal directions in which to respectively move one or more of the moveable light emitting modules associated with the identified obstruction to achieve the respective positions at which the corresponding areas of the surgical site are illuminated by the emitted predetermined amount of light of the one or more of the light emitting elements of the moveable light emitting modules without inhibition by the obstruction.

18. The apparatus of claim 8, wherein the control unit is further configured to determine optimal directions in which to respectively move one or more of the moveable light emitting modules associated with the identified obstruction to achieve the respective positions at which the corresponding areas of the surgical site are illuminated by the emitted predetermined amount of light of the one or more of the light emitting elements of the moveable light emitting modules without inhibition by the obstruction, and
wherein the control unit is further configured to move the motor gears of the one or more moveable light emitting modules in the optimal directions to move the one or more moveable light emitting modules to the respective positions.

19. The apparatus of claim 1, wherein the control unit comprises a user interface configured to permit user input of the predetermined amount of light to be emitted from each of the light emitting elements to illuminate the corresponding area of the surgical site.

20. A surgical lighting apparatus, comprising:
a lighthead configured to illuminate a surgical site disposed in the surgical environment, the lighthead comprising a plurality of light emitting modules, each of the light emitting modules comprising a plurality of light emitting elements positioned on a front side thereof, each of the light emitting elements being configured to emit a predetermined amount of light from the light emitting modules to illuminate a corresponding area of a surgical site, the light emitting modules being comprised of a plurality of stationary light emitting modules and a plurality of moveable light emitting modules;
one or more sensors configured to collect data regarding an amount of the emitted light from each of the light emitting elements that is delivered to the corresponding area of the surgical site, the sensors being further configured to transmit the collected data; and a control unit configured to receive the transmitted data from the sensors and identify, from the received data, an obstruction inhibiting respective delivery of the predetermined amount of light from one or more of the light emitting elements of the moveable light emitting modules to the corresponding areas of the surgical site, the control unit being further configured to control movement of one or more of the moveable light emitting modules to respective positions at which the corresponding areas of the surgical site are illuminated by the emitted predetermined amount of light of the one or more of the light emitting elements of the moveable light emitting modules without inhibition by the obstruction.

* * * * *